United States Patent
Tam

(10) Patent No.: US 10,228,330 B2
(45) Date of Patent: Mar. 12, 2019

(54) PRECIOUS STONE TESTING DEVICE

(71) Applicant: Jubilee Diamond Instrument (S) Pte. Ltd., Singapore (SG)

(72) Inventor: Kui Lim Tam, Singapore (SG)

(73) Assignee: Jubilee Diamond Instrument (S) Pte. Ltd., Singapore (SG)

( * ) Notice: Subject to any disclaimer, the term of this patent is extended or adjusted under 35 U.S.C. 154(b) by 0 days.

(21) Appl. No.: 16/128,610

(22) Filed: Sep. 12, 2018

(65) Prior Publication Data

US 2019/0011373 A1    Jan. 10, 2019

Related U.S. Application Data

(63) Continuation of application No. PCT/IB2016/053208, filed on Jun. 1, 2016.

(51) Int. Cl.
*G01N 21/00* (2006.01)
*G01N 21/87* (2006.01)
*G01N 21/31* (2006.01)

(52) U.S. Cl.
CPC .............. *G01N 21/87* (2013.01); *G01N 21/31* (2013.01); *G01N 2201/0636* (2013.01)

(58) Field of Classification Search
CPC ........ G01N 21/87; G01N 21/31; G01N 27/04; G01N 27/26; G01N 27/28; G01N 33/385; G01N 33/381; G01N 33/24; G01J 1/16; G01R 27/02; G01R 27/08; G01R 27/12
See application file for complete search history.

(56) References Cited

U.S. PATENT DOCUMENTS

| | | |
|---|---|---|
| 2,789,430 A | 4/1957 | Sinclaire |
| 4,255,962 A | 3/1981 | Ashman |
| 4,344,315 A | 8/1982 | Moxon et al. |
| 4,364,677 A | 12/1982 | Ashman |
| 4,394,580 A | 7/1983 | Gielisse |
| 4,488,821 A | 12/1984 | Wenckus |
| 5,801,819 A | 9/1998 | Spear et al. |
| 5,835,205 A | 11/1998 | Hunter et al. |
| 5,883,389 A | 3/1999 | Spear et al. |
| 5,955,735 A | 9/1999 | Coleman |
| 6,265,884 B1 | 7/2001 | Menashi et al. |
| 6,439,766 B1 | 8/2002 | Nelson |

(Continued)

FOREIGN PATENT DOCUMENTS

| | | |
|---|---|---|
| WO | 8001414 | 7/1980 |
| WO | 2015007873 | 1/2015 |

OTHER PUBLICATIONS

Gems & Gemology; Article entitled: "Synthetic Moissanite: A New Diamond Substitute", published Winter 1997, 16 pgs.

(Continued)

*Primary Examiner* — Abdullahi Nur
(74) *Attorney, Agent, or Firm* — Taylor English Duma LLP

(57) ABSTRACT

A gemstone testing apparatus with an apparatus body, a reflector housing with a light reflective layer at its interior surface, a transparent housing portion that is transparent for ultraviolet light, and a detector probe that is protruding from the transparent housing portion. An UV light emitter is provided within the reflector housing, which is adapted for directing the UV light through the transparent housing portion into the vicinity of a tip of the detector probe.

17 Claims, 5 Drawing Sheets

(56) References Cited

U.S. PATENT DOCUMENTS

| | | | |
|---|---|---|---|
| 7,126,351 | B2 | 10/2006 | Claus |
| 7,259,839 | B2 | 8/2007 | Sivovolenko |
| 7,362,109 | B2 | 4/2008 | Loginov |
| 7,382,445 | B2 | 6/2008 | Sasian et al. |
| 8,278,906 | B2 | 10/2012 | Loginov et al. |
| 8,564,316 | B2 | 10/2013 | Kessler et al. |
| 8,749,253 | B2 | 6/2014 | Kessler et al. |
| 9,395,350 | B2 | 7/2016 | Kessler et al. |
| 10,161,878 | B2 | 12/2018 | Tam |
| 2001/0023925 | A1 | 9/2001 | Smith |
| 2004/0008888 | A1 | 1/2004 | Patton et al. |
| 2006/0044823 | A1 | 3/2006 | Wong et al. |
| 2006/0087306 | A1 | 4/2006 | Loginov |
| 2006/0098187 | A1 | 5/2006 | Claus |
| 2012/0007619 | A1 | 1/2012 | Zhu et al. |
| 2012/0059619 | A1 | 3/2012 | Zhu et al. |
| 2012/0274751 | A1 | 11/2012 | Smith et al. |
| 2014/0337035 | A1 | 11/2014 | Kessler et al. |
| 2015/0015877 | A1* | 1/2015 | Smith .................. B07C 5/3425 356/300 |
| 2015/0091593 | A1* | 4/2015 | Zhu ........................ G01N 21/87 324/693 |
| 2015/0219567 | A1 | 8/2015 | Sim et al. |
| 2018/0238811 | A1 | 8/2018 | Tam |

OTHER PUBLICATIONS

Gems & Gemology; Symposium proceedings issue entitled: "Proceedings of the Third International Gemological Symposium", published Fall 1999, 185 pgs.

Tam, Kui Lim; International Preliminary Report for Patentability for PCT/IB2016/054071, filed Jul. 7, 2016, dated Nov. 28, 2017, 4 pgs.

Tam, Kui Lim; International Search Report and Written Opinion for PCT/IB2016/054071, filed Jul. 7, 2016, dated Oct. 26, 2016, 11 pgs.

Tam, Kui Lim; Notice of Allowance for U.S. Appl. No. 15/751,529, filed Feb. 9, 2018, dated Aug. 23, 2018, 14 pgs.

Tam, Kui Lim; International Search Report for PCT/IB2016/053208, filed Jun. 1, 2016, dated Feb. 28, 2017, 3 pgs.

Zeiss; Article entitled: "Education in Microscopy and Digital Imaging", published as early as Dec. 23, 2008, located at <https://web.archive.org/web/20081223034455/http://zeiss-campus.magnet.fsu.edu/articles/lightsources/tungstenhalogen.html>, 9 pgs.

Tam, Kui Lim; Supplemental Notice of Allowance for U.S. Appl. No. 15/751,529, filed Feb. 9, 2018, dated Sep. 11, 2018, 12 pgs.

Tam, Kui Lim; Notice of Allowance for U.S. Appl. No. 15/751,529, filed Feb. 9, 2018, dated Oct. 3, 2018, 13 pgs.

Tam, Kui Lim; International Preliminary Report on Patentability for PCT/IB2016/053208, filed Jun. 1, 2016, dated Oct. 11, 2018, 7 pgs.

Tam, Kui Lim; Issue Notification for U.S. Appl. No. 15/751,529, filed Feb. 9, 2018, dated Dec. 5, 2018, 1 pg.

Tam, Kui Lim; Non-Final Office Action for U.S. Appl. No. 16/176,059, filed Oct. 31, 2018, dated Jan. 2, 2019, 15 pgs.

* cited by examiner

PRECIOUS STONE TESTING DEVICE

CROSS-REFERENCE TO RELATED APPLICATIONS

This application is a continuation of PCT International Application No. PCT/IB2016/053208, with an international filing date of Jun. 1, 2016, the disclosure of which is incorporated herein by this reference in its entirety.

BRIEF SUMMARY

The subject matter of the present specification relates to a precious stone testing apparatus and, more particularly, to a precious stone testing apparatus with an ultraviolet LED light unit that provides illumination at the conductive probe used for determining thermal and/or electrical conductivity when the conductive probe contacts the tested specimen or object.

A gemstone tester provides a convenient means for the identification of gemstones such as diamond, moissanite and other precious stones. In general, a gemstone tester comprises of a testing probe for determining the thermal conductivity and, if necessary, the electrical conductivity of the gemstone in order to classify the gemstone by its physical properties.

A gemstone tester can be used to differentiate between diamonds and other minerals using thermal conductivity and electrical conductivity tests. The thermal conductivity test separates diamond from all other gemstones, except moissanite, since diamonds conduct heat significantly greater than all other gemstones, except moissanite. White sapphire is thermally conductive, yet not as conductive as diamond and moissanite and therefore it can be easily separated. Since moissanite conducts electricity in varying degrees and colorless diamonds generally are isolators, the electrical conductivity test separates the vast majority of moissanite from colorless diamond.

There are certain types of moissanite that possess high electrical resistance. However, the electrical resistance may be reduced by irradiating the moissanite under test with an ultraviolet light. Therefore, based upon readings from the electrical conductivity tests, colorless diamonds and moissanite may be distinguished. Colored diamonds, on the other hand, may also in certain cases possess electrical conducting properties that are comparable to that of moissanite.

Among others, the current specification discloses an improved gemstone testing apparatus, which can provide an improved distinction between diamond and moissanite. The gemstone testing apparatus is also referred to as "gemstone testing device".

The gemstone testing apparatus comprises an apparatus body, which contains or encloses electronic circuitry. The electronic circuitry is provided to control the operation of the apparatus. More specifically, it is provided to evaluate sensor signals, draw electrical power, generate indicator signals, and receive user actions and user input.

The electronic circuitry is connected to a power supply unit, such as a battery or a socket connection. Furthermore, an indicator region can be provided at a top surface of the apparatus body for indicating, among others, the type of a detected specimen, an operating status and a battery status.

A head portion of the gemstone testing apparatus comprises a detector probe, a reflective housing and a transparent housing portion and an UV light emitter.

The transparent housing portion is transparent for at least a spectral portion of the UV light that is emitted by the UV light emitter. This is achieved by using an UV transparent material. Preferentially, the UV transparent material is an UV transparent plastics material such as polymethylpentene, UV transparent PMMA or UVT acrylic. In other embodiments, the UV transparent material may also comprise an UV transparent glass material or an UV transparent crystalline material. For example, an UV transparent material of the transparent housing portion may have a transmissivity of 80% or above for wavelengths of 365 nanometers to 420 nanometers.

The transparent housing portion is provided adjacent to the reflector housing. In particular, the transparent housing portion can be connected or attached to the reflector housing by an adhesive bond or by a form fit, such as a snap-fit. Specifically, it can be inserted into an opening at a front end of the reflector housing, wherein the opening of the reflector can be a circular opening. The transparent housing portion may have a lens shape. For example, the transparent housing portion can be shaped as a convex lens, which can bundle the radiation emitted from the UV light emitter.

An interior surface of the reflector housing is provided or coated with a light reflective layer. In particular, the layer is reflective for ultraviolet light in the near UV spectral range, which is emitted by the UV light emitter. For example, the light reflective layer can comprises a metallic material, which is provided by electroplating.

The detector probe is provided for contacting a surface of a specimen and for performing heat conductivity and electrical conductivity tests of the specimen. In particular, the detector probe can comprise a rod.

The detector probe protrudes from the transparent housing portion and extends through the transparent housing portion. In particular, the detector probe can be provided in a central portion of the transparent housing portion, for example it can be provided at a tip of the transparent housing portion.

An ultraviolet (UV) light emitter is provided within the reflector housing. The reflector housing is provided for directing ultraviolet light of the UV light emitter through the transparent housing portion into the vicinity of a tip of the detector probe, thereby affecting a measurement of the detector probe. For example, the UV light can irradiate a region with a radius of about 1 cm around the tip of the detector probe, but the region may also be smaller or larger.

The UV light emitter is provided within a chamber that is bounded or defined by the transparent housing portion, the reflector housing and the apparatus body. Preferentially the UV light emitter is provided by an UV light emitting diode (LED).

The detector probe and the UV light emitter are connected to the electronic circuitry. The electronic circuitry comprises a conductivity sensing circuitry that is connected to the detector probe and to a processing unit, such as a microcontroller. The processing unit is operative to turn on the UV light emitter and to perform a subsequent conductivity measurement using the conductivity sensing circuitry, which is also referred to as "electrical conductivity circuit".

The subsequent conductivity measurement is performed after the UV light is turned on and while a moissanite material can still be excited by the UV light and thereby have an enhanced conductivity. Typically, the conductivity test takes place during an illumination with UV light but it could also take place shortly after the UV light is turned on.

In one embodiment, the processing unit and the conductivity sensing circuitry are provided as separate components on a printed circuit board.

The positioning of the detector probe at the transparent housing, and in particular a positioning at a central position of the transparent housing provides an effective illumination with UV light. UV light of the UV light emitter that passes through the transparent housing portion can illuminate the specimen surface around a contact region between the probe and the specimen in an effective way and such that an intensity of the UV irradiation around the contact region can be increased.

The above-mentioned light reflective layer of the reflector housing can further enhance UV light irradiation by directing UV light rays of the UV light emitter towards the transparent housing portion by single or multiple reflections. Thereby, the intensity of the UV irradiation through the transparent housing portion is further increased.

Furthermore, in a gemstone testing apparatus according to the present specification the UV light emitter can be dust protected by the housing and a heat radiation from the UV light emitter can be held back, thereby reducing a heating up of the specimen.

The UV light emitter can be provided such that the connection legs are connected to the electronic circuitry but the rest of the diode is provided at a distance from other parts. Furthermore, the UV light emitter can be positioned such that a direction of maximum radiation intensity points towards the transparent housing portion, towards the tip of the transparent housing portion or towards a location next to the tip of the transparent housing portion.

The UV light emitter can be positioned offset to a central axis of the device, for example when the detector probe is positioned at the central axis.

To increase the intensity of the reflected radiation even further, the back surface of a chamber that is defined between the transparent housing portion, the reflector housing and the apparatus body, and in which the UV light emitter is provided, can be provided with a light reflective layer. The back surface is defined or formed at a boundary between the reflector housing and the apparatus body.

The reflector housing can be made such that an interior surface of the reflector housing is essentially entirely covered with the light reflective layer. By way of example, this can be achieved by electroplating the reflector housing. In particular, the reflector housing can be made opaque to UV light by using a suitable material and/or by the reflective surface layer.

In one embodiment, the transparent housing portion is conically tapered from the reflector housing towards a tip end of the transparent housing portion, thereby allowing UV light to exit in a predetermined range of directions. Furthermore, the reflector housing can be conically tapered from the apparatus body or an attachment region to the apparatus body towards the transparent housing portion.

In particular, the dimensions of the reflector housing and the transparent housing portion can be made such that a longitudinal dimension of the reflector housing along a longitudinal axis of the gemstone testing device is at least 3 to 4 times as long as the longitudinal dimension of the transparent housing portion.

In a further aspect, the present specification discloses a head portion for attachment to an apparatus body of a gemstone testing apparatus.

The head portion comprises a reflector housing, an interior surface of which is provided with a light reflective layer, and in particular a layer, which is reflective for near UV light. Furthermore, the head portion comprises a transparent housing portion that is attached to the reflector housing and that is transparent for ultraviolet light in the near UV region of an UV light emitter that is provided for detecting moissanite. A detector probe protrudes from the transparent housing portion. The detector probe has connections for connecting to electronic circuitry of the gemstone testing apparatus through connection terminals. The detector probe is a thermocouple provided by two constantan wires, which are connected to the connection terminals of the electronic circuitry of the gemstone testing apparatus in an assembled state.

Furthermore, the head portion according to the present specification can comprise an ultraviolet light emitter that is provided within the reflector housing, and which has electrical connections for connecting to the electronic circuitry of the gemstone testing apparatus.

In a further aspect, the current specification discloses a method of production for a gemstone testing apparatus. According to this method, a transparent housing portion with a detector probe is provided. An interior surface of a reflector housing is coated with a light reflective layer, for example by electroplating.

The transparent housing portion is attached to the reflector housing, for example by melting a connecting region, such as plastic welding, by gluing or by form fit. An apparatus body is provided and an UV light emitter is connected to electronic circuitry of the apparatus body. Furthermore, a detector probe is connected to the electronic circuitry and the reflector housing, which is attached to the apparatus body, for example by using a plastic holder assembly or support.

These and other features and aspects of the various embodiments will become apparent upon reading the following Detailed Description and reviewing the accompanying drawings.

BRIEF DESCRIPTION OF THE DRAWINGS

The subject matter of the present specification is now explained in further detail with reference to the following Figures in which.

DETAILED DESCRIPTION

In the following description, details are provided to describe the embodiments of the specification. It shall be apparent to one skilled in the art, however, that the embodiments may be practised without such details.

Figure 1A:
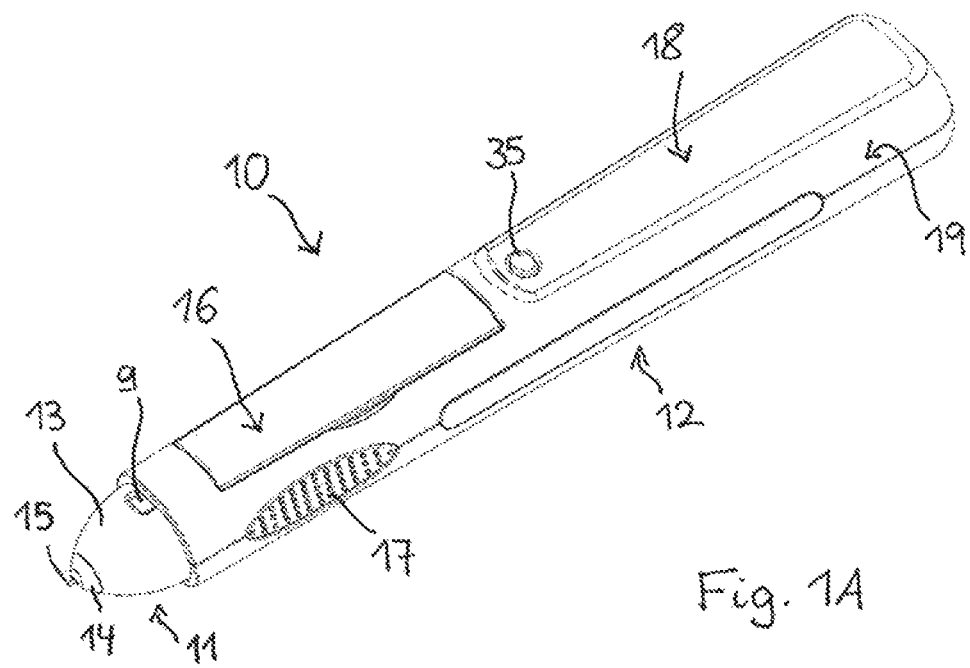
FIG. 1A shows a perspective view of a gemstone testing device.

FIG. 1A shows a perspective view of a gemstone testing apparatus 10 according to the current specification. The gemstone testing device 10 comprises a head portion 11 and an apparatus body 12. The head portion 11 comprises a cylindrical reflector portion 13, which is provided adjacent to the apparatus body 12, and a transparent cylindrical portion 14, which is provided at a tip of the head portion 11. The transparent cylindrical portion 14 is also referred to as "transparent housing portion" and the reflector portion 13 is also referred to as "reflector housing".

A detector probe 15, which is shaped in the form of a rod, extends through the transparent cylindrical portion 14. The head portion 11 tapers from a region in which the head portion 11 is attached to the apparatus body 12 towards the detector probe 15. A catch 9 allows attachment of an external cap, which is not shown in FIG. 1A, using a snap-fit.

Figure 2:
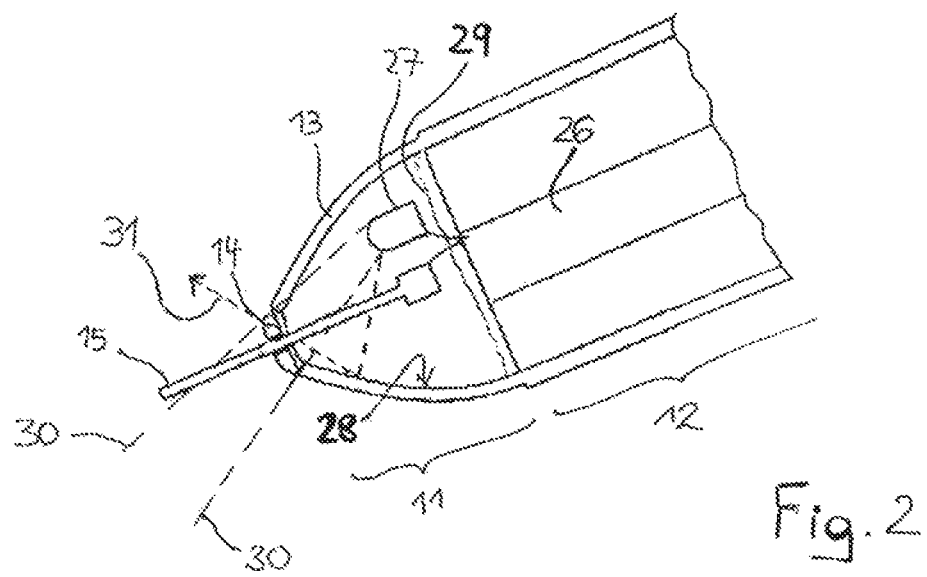
FIG. 2 shows a partial cross section view of a front portion of the device of one of the FIGS. 1A to 1C.

The transparent cylindrical portion 14 is made from an UV transparent plastics material, such as polymethylpentene or UV transparent PMMA in order to allow the transmission of UV light from an UV light source, which is provided inside the head portion 11 and which is shown in FIG. 2.

The apparatus body 12 comprises an indicator region 16, which is provided on a top surface 18 of the apparatus body 12, and two grip indentations 17, which are provided at opposite side surfaces 19 of the apparatus body 12. The apparatus body 12 also comprises electronics components and a power supply, which are not shown in FIG. 1A. The electronics components are connected to the detector probe 15 and to indicator lights of the indicator region 16, which are not shown in FIG. 1A. As an alternative or in addition to the indicator lights 21, a display panel 20 can be provided, as shown in FIG. 1C.

The power supply comprises a battery compartment for one or more batteries, which are not shown in FIG. 1A. Optionally, a connection for external power supply and corresponding electronic circuitry can be provided as well. An on/off switch 35 is provided for switching the electrical power of the device.

The head portion 11 of FIG. 1A is provided with a round cylindrical shape that is centered around a longitudinal axis of the gem testing apparatus. Other shapes, such as a pyramidal shape, are also possible. Such alternative shapes are shown, by way of example, in the embodiments of FIGS. 1B and 1C and of the FIGS. 5 to 8. Furthermore, the shape of the head region can be asymmetric such that the tip of the head portion is offset with respect to the central axis and is pointing in a downward direction.

Figure 1B:
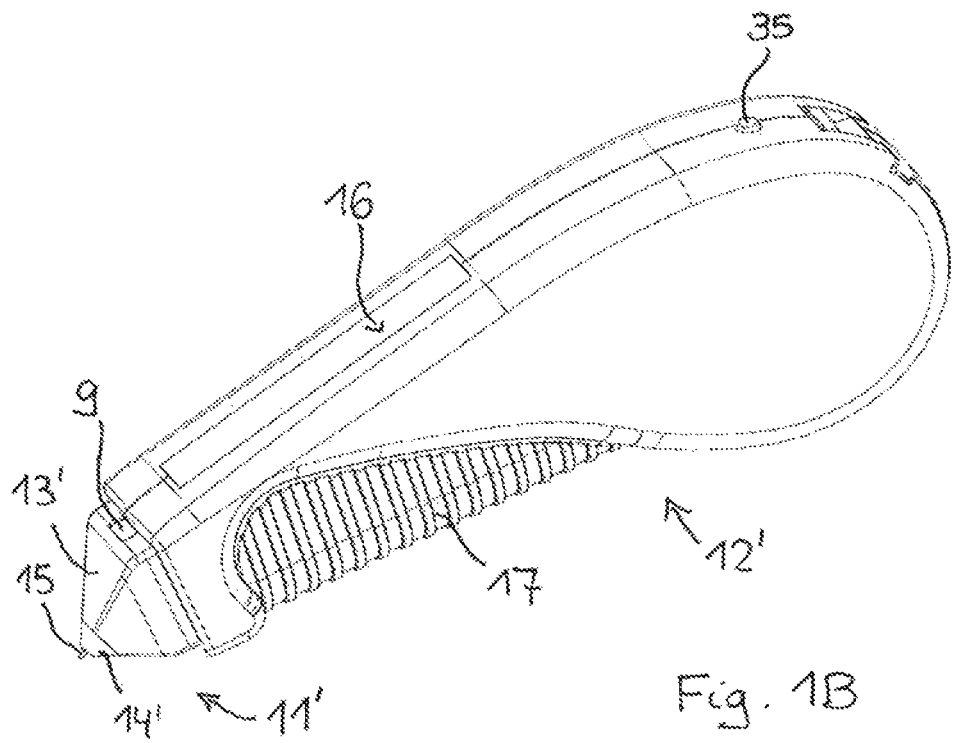
FIG. 1B shows a perspective view of a further embodiment of a gemstone testing device.
Figure 1C:
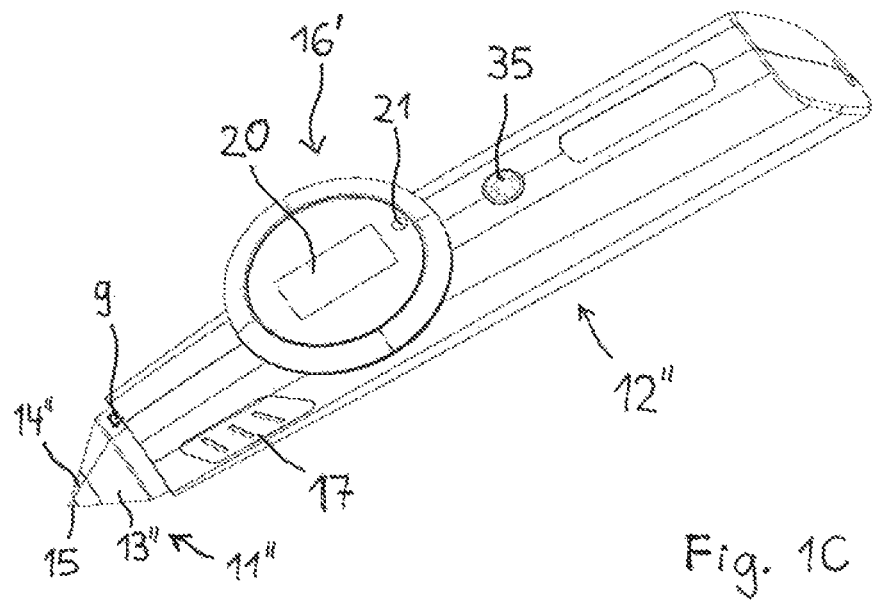
FIG. 1C shows a perspective view of a further embodiment of a gemstone testing device.

The FIGS. 1B and 1C show further embodiments of a gemstone testing device 10', 10". These embodiments are similar to the embodiment of FIG. 1A and can be used together with the same or similar electronic circuitry as the embodiments of FIG. 1A. Similar parts have the same or similar reference numbers.

The outer shape of the head regions 11' and 11" in FIGS. 1B and 1C has the form of a two-step square pyramid. Furthermore, the head region 11' in FIG. 1B is slightly slanted downwards, which makes it possible to hold the device more towards a horizontal position when the probe touches the surface of a specimen.

Figure 7:
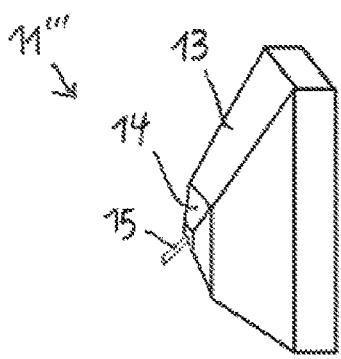
FIG. 7 shows a third alternative shape of a head portion of the gemstone testing device of one of the FIGS. 1A to 1C.
Figure 8:
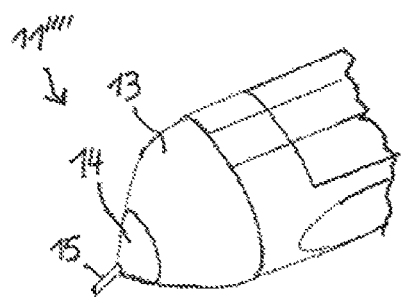
FIG. 8 shows a fourth alternative shape of a head portion of the gemstone testing device of one of the FIGS. 1A to 1C.

Different from the embodiment of FIG. 1A and similar to the head shapes shown in FIGS. 7 and 8, the head region 11' is slanted downwards, such that the testing apparatus 10' can be held in a more horizontal position while the detector probe 15 contacts a surface of the specimen.

FIG. 1C shows a perspective view of a further embodiment of a gemstone testing device 10. The display region 16" of the embodiment of FIG. 1C comprises a liquid-crystal display (LCD) 20 and the overall shape of the gemstone testing device and the outer shape of the head portion is different from the embodiment of FIG. 1A. Furthermore, an indicator light 21 is provided next to the LCD 20.

FIG. 2 shows a cross section view of a front portion of the gemstone testing apparatus 10 of FIG. 1A, which includes the head portion 11 and part of the apparatus body 12. The description of FIG. 2 also applies to the similar embodiments of FIGS. 1B and 1C.

As shown in FIG. 2, the detector probe 15 is electrically connected to a printed circuit board 26, which is provided inside the apparatus body 12. The detector probe 15 may contain multiple sensors, which are separately connected to the printed circuit board 26. An UV LED (light emitting diode) 27 is provided inside the cylindrical reflector portion 13 of the head portion 11. A layer of an UV reflecting material covers an inner surface 28 of the cylindrical reflector portion 13. In particular, the inner surface 28 can be coated by a metal layer, which is provided by an electroplating process.

According to a further embodiment a back surface 29, which is located at the boundary of the head portion 11 and the apparatus body 12, is also coated by the UV reflecting material. Furthermore, the detector probe 15, or an interior portion thereof, may also be coated by UV reflecting material. In FIG. 2 first dashed lines 30 indicate boundaries of an irradiation zone of primary LED light. A second dashed line 31 indicates a radiation beam of reflected LED light.

During a production process of the gemstone testing device 10, the cylindrical reflector portion 13 may be molded and electroplated as a separate part which is then fixed to the apparatus body 12 by snap fit or by molding the cylindrical portion 13 onto the apparatus body 12 through a thermal process, thereby fusing the cylindrical reflector portion 13 and the apparatus body 12 into an integral part.

Figure 3:
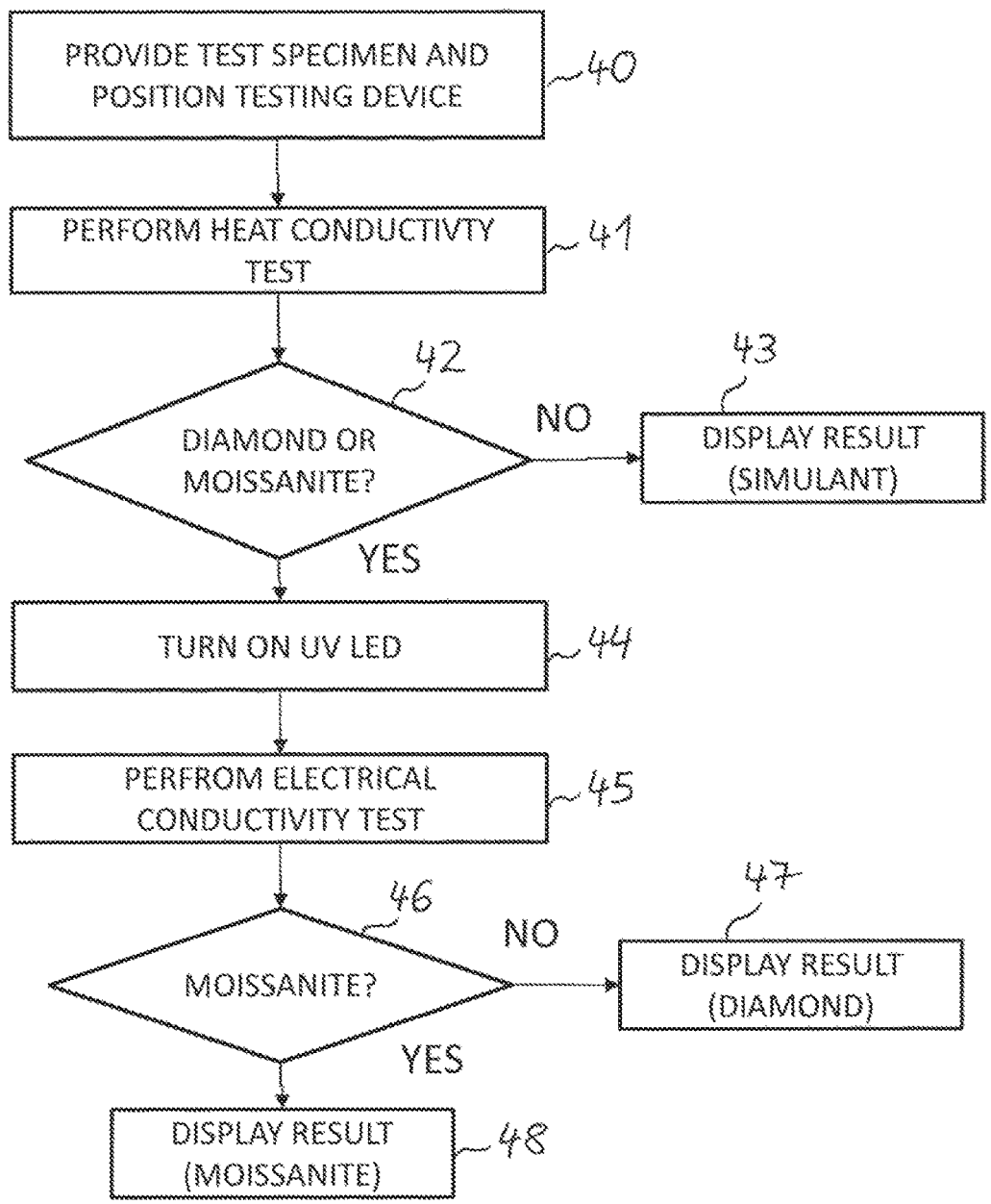
FIG. 3 shows a flow diagram illustrating a mode of operation of the gemstone testing device of one of the FIGS. 1A to 1C.

FIG. 3 shows a flow diagram, which provides an example of an operation sequence of the gemstone testing device 10 of one of the FIGS. 1A to 1C. The method of FIG. 3 is performed by electronic circuitry of the gemstone testing apparatus, such as the diagram shown in FIG. 4.

In a method step 40, a test specimen is held in position and the gemstone testing device is positioned on the specimen. In particular, the detector probe can be provided on a surface of the specimen. By way of example, the specimen can be held in position by holding it by placing it on a holder or having it mounted on a ring.

In a testing step 41, a thermal conductivity test is performed. For example, this test can be performed by bringing the specimen surface into contact with the detector probe 15, which is hotter than the specimen surface, and by measuring the timing and amount of heat loss on the detector probe 15 after contacting the specimen under test. According to a preferred method, the detector probe 15 is heated up first and a dissipation of heat onto the specimen is measured.

In a decision step 42, the electronic circuitry of the gemstone testing device 10 evaluates sensors signals and provide an automatic decision if the specimen falls under the category of diamond or moissanite. In particular, the thermal conductivity results obtained in the previous testing step 41 can be used to arrive at this decision.

Furthermore the thermal conductivity measurement or a separate electrical measurement can be used to automatically detect if the user has accidentally touched a metal surface and to provide a corresponding acoustic and/or optic signal.

If, in decision step 42, it is decided that the specimen consists of a material other than diamond or moissanite, the result is displayed accordingly in the display area 16 in display step 43, for example by lighting up an indicator light 21 or by showing a display symbol on the display panel 20, wherein the symbol can also be a text.

If, in decision step 42, it is decided that the specimen is a diamond or moissanite, the UV LED is turned on in method step 44 and the detector probe 15 is used in testing step 45 to perform an electrical conductivity test during an UV illumination of the specimen or shortly after the specimen has been illuminated. For example, a dissipation rate a DC current or an attenuation of an applied AC signal can be used to determine the electrical conductivity.

In particular, the gemstone testing device 10 can be configured such that the UV light only lights up when the detector probe 15 is into contact with a specimen and when it is determined that the specimen is either diamond or moissanite. Thereby it is possible to save energy and to avoid a hazardous exposure to UV radiation.

In addition to displaying optical signals in the display area, the gemstone testing device 10 may also produce corresponding acoustic signals. A buzzer 33 connected to the microcontroller 34, is provided for generating an acoustic output signal.

The gemstone testing device 10 also comprises an infrared transmitting LED 32 for sending the test result to another electronic device for displaying more details.

The result of the electrical conductivity test in testing step 45 is used in decision step 46 to automatically determine whether the specimen is a diamond or a moissanite. If it is determined that the specimen is not a moissanite, the specimen is determined to be diamond. The result is displayed accordingly in the display area 16 in display step 47, for example by lighting up a display light 21 or by displaying a display symbol on the display panel 20, wherein the symbol can also be a text.

If, on the other hand, it is determined in decision step 46 that the specimen is a moissanite, the result is displayed accordingly in the display area 16 in display step 48, for example by lighting up a display light 21 or by displaying a display symbol on the display panel 20, wherein the symbol can also be a text.

Figure 4:
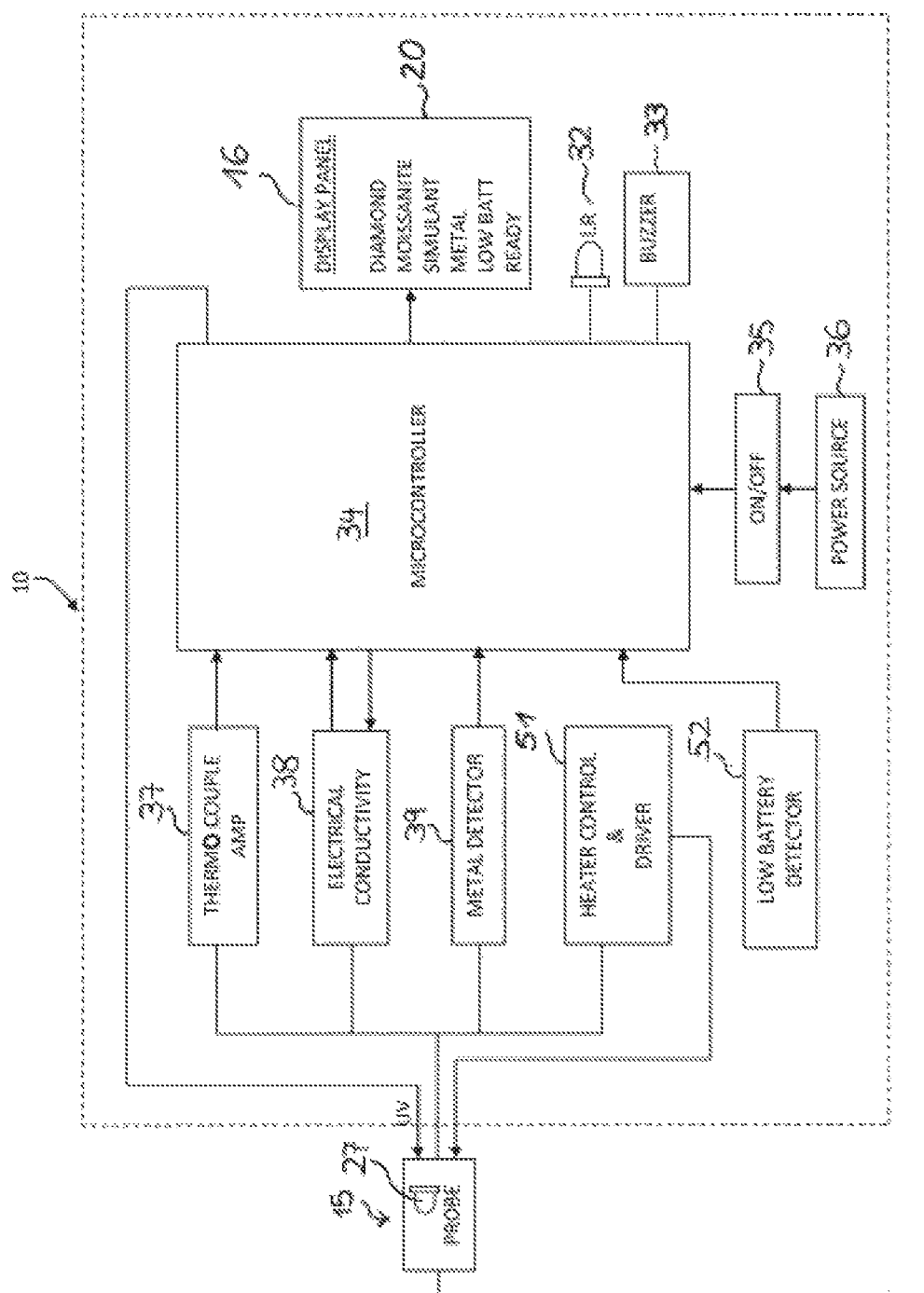
FIG. 4 shows an electronic block diagram of the gemstone testing device of one of the FIGS. 1A to 1C.

The display region 16 provides visual indications of the device status "Ready", the detected materials "Metal", "Moissanite", "Simulant", "Diamond" and of the battery status "low battery". The visual indications can be provided by a display panel 20, as indicated in FIG. 4. Alternatively, the visual indication can also be provided by light emitters.

The display panel 20 may be a color or a monochrome screen display, such as a LCD, or by an OLED display. The light emitters may be provided by LEDs with suitably chosen colors. The display panel 20 indicators, display lights 21 and the UV LED 27 are controlled by individual output port pins of the microcontroller 34.

Furthermore, a buzzer 33 is connected to the microcontroller 34 for emitting acoustic indicator signals. For example, according to one embodiment the microcontroller 34 is operative to generate specific sounds for metal detection, simulant detection, moissanite detection and diamond detection.

The detector probe 15 is connected to various sensing units, such as a thermocouple amplifier 37, an electrical conductivity circuit 38, a metal detector circuit 39 and a heater control and driver 51. The sensing units are in turn connected to a microcontroller 34. In FIG. 4, "probe" refers to the sensing rod and to the portion of the housing in which the UV LED 27 is provided. The assembly of the sensing extension and the portion of the housing to which it is connected may also be referred as "probe assembly".

Heating components are provided for carrying out the thermal conductivity test. According to one specific realization, the heating components include a heating resistor, and a measuring thermistor. The heating components are providing for heating the specimen and for monitoring the temperature of the heated probe. The heater control and driver unit 51 comprises circuitry for detecting heat conductivity.

The electrical conductivity circuit 38 comprises circuitry for controlling and performing a test for electrical conductivity. Similarly, the metal detector circuit 39 comprises circuitry for detecting a metal material. The electrical conductivity test and the metal detection test can be realized using an electrical contact. Furthermore, the test can be realized using DC and/or AC signals.

An infrared transmitting LED 32 is provided for sending the test results to a secondary electronic device for displaying more details. The infrared transmitting LED 32 is connected to other components in the electronic circuitry, which are in turn connected to the microcontroller 34. In the embodiment of FIG. 4, the infrared LED 32 is provided using a serial interface. The data signals are transmitted via UART peripheral of the microcontroller 34 to a secondary electronic device.

The microcontroller 34 comprises A/D converters for converting analogue measuring signals into digital values, which are then processed by the microcontroller 34 to obtain a result that indicates of which material the specimen is made of.

According to the embodiment of FIG. 4, a low battery detector circuit 52 is provided to measure and monitor the voltage of the battery source. The "low battery" indicator light 21 will light up when battery voltage is low. The on/off switch 35 and a power source 36 are indicated in the bottom of FIG. 4. By way of example, the power source can be provided by a battery or by a connection to an external power source.

FIGS. 5 to 8 show alternative head shapes for use in the gemstone testing devices of FIG. 1A, 1B or 1C. Similar parts have the same or similar reference number. The prime symbols "'" are not related to those in FIG. 1A to 1C.

Figure 5:
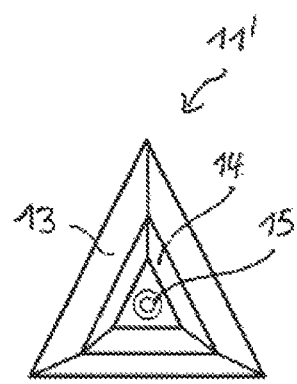
FIG. 5 shows a first alternative shape of a head portion of the gemstone testing device of one of the FIGS. 1A to 1C.
Figure 6:
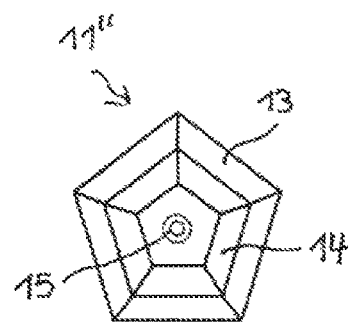
FIG. 6 shows a second alternative shape of a head portion of the gemstone testing device of one of the FIGS. 1A to 1C.

FIG. 5 shows a first alternative shape of a head portion 11', according to which the head portion 11' is shaped as a trigonal pyramid with a central plateau. FIG. 6 shows a second alternative shape of a head portion 11", which can be used in the gemstone testing devices according to one of the FIGS. 1A to 1C.

FIG. 7 shows a third alternative shape of a head portion 11''' according to which the head portion 11''' is shaped as an asymmetric quadrilateral pyramid with a central plateau.

FIG. 8 shows a fourth alternative shape of a head portion 11'''' according to which the head portion 11'''' is shaped similar to the embodiment of FIG. 1A, but is slanted in a downwards direction perpendicular to a longitudinal axis of the device.

The whole transparent housing portion 14 is transparent throughout. This applies also to the embodiments of FIGS. 1A to 1C as well as to the head portions of FIGS. 5 to 7.

In a more limiting sense, the term "UV light" may also refer to near ultraviolet from 300 to 420 nm wavelength only or it may refer to near and middle ultraviolet light only with wavelengths in the range between 200 and 420 nm. Furthermore, the UV light emitter may also emit light in the visible violet and blue spectrum and this emission in the visible violet and blue spectrum may also be used for the conductivity measurement.

Although the above description contains much specificity, these should not be construed as limiting the scope of the embodiments but merely providing illustration of the foreseeable embodiments. Especially the above stated advantages of the embodiments should not be construed as limiting the scope of the embodiments but merely to explain possible achievements if the described embodiments are put into practice. Thus, the scope of the embodiments should be determined by the claims and their equivalents, rather than by the examples given.

The embodiments of the present specification can also be described with the following lists of elements being organized into items. The respective combinations of features which are disclosed in the item list are regarded as independent subject matter, respectively, that can also be combined with other features of the present specification.

1. A gemstone testing apparatus comprising
 an apparatus body, the apparatus body enclosing electronic circuitry,
 an UV light emitter for generating ultraviolet light,
 a reflector housing, an interior surface of the reflector housing being provided with a light reflective layer,
 a transparent housing portion, the transparent housing portion being transparent for ultraviolet light, the transparent housing portion being provided adjacent to the reflector housing,
 a detector probe, the detector probe protruding from the transparent housing portion,
 wherein the UV light emitter is provided within the reflector housing and the reflector housing is provided for directing the ultraviolet light of the UV light emitter through the transparent housing portion into the vicinity of a tip of the detector probe, and
 wherein the detector probe and the UV light emitter are connected to the electronic circuitry, the electronic circuitry comprising a conductivity sensing circuitry that is connected to the detector probe and to a processing unit, the processing unit being operative to turn on the UV light emitter and to perform a subsequent conductivity measurement using the conductivity sensing circuitry.

2. The gemstone testing apparatus of item 1, wherein the UV light emitter capable of emit-ting light with a wavelength of 365 nm to 420 nm.

3. The gemstone testing apparatus of one of the items 1 to 2, wherein the detector probe is provided at an end portion of the transparent housing portion.

4. The gemstone testing apparatus according to one of the items 1 to 3, wherein a back surface of a chamber that is defined between the transparent housing portion, the reflector housing and the apparatus body is provided with a light reflective layer.

5. The gemstone testing apparatus according to one of the items 1 to 4, wherein an interior surface of the reflector housing is essentially entirely covered with the light reflective layer.

6. The gemstone testing apparatus according to one of the preceding items, wherein the reflective layer is provided by electroplating.

7. The gemstone testing apparatus according to one of the preceding items, the gemstone testing apparatus comprising a display region that is connected to the processing unit.

8. The gemstone testing apparatus according to item 7, wherein the display region comprises indicator LEDs.

9. The gemstone testing apparatus according to item 7 or 8, wherein the display region comprises a LCD.

10. The gemstone testing apparatus according to one of the preceding items, wherein the UV light emitter is positioned at a distance from other parts of the gemstone testing apparatus.

11. The gemstone testing apparatus according to one of the preceding items, wherein the transparent housing portion is conically tapered from the reflector housing towards a tip end of the transparent housing portion.

12. The gemstone testing apparatus according to one of the preceding items, wherein the reflector housing is conically tapered from the apparatus body towards the transparent housing portion.

13. The gemstone testing apparatus according to one of the preceding items, wherein a longitudinal dimension of the reflector housing is at least three to four times as long as a longitudinal dimension of the transparent housing portion.

14. The gemstone testing apparatus according to one of the preceding items, the electronic circuitry comprising a temperature sensing circuitry that is connected to the detector probe and to the processing unit.

15. A head portion for a gemstone testing apparatus, the head portion comprising
 a reflector housing, an interior surface of the reflector housing being provided with a light reflective layer,
 a transparent housing portion, the transparent housing portion being attached to the reflector housing, the transparent housing portion being transparent for ultraviolet light,
 a detector probe, the detector probe protruding from the transparent housing portion, the detector probe having connections for connecting to electronic circuitry of the gemstone testing apparatus.

16. The head portion of item 15, comprising
 an UV light emitter, the UV light emitter being provided within the reflector housing, and the UV light emitter having connections for connecting to the electronic circuitry.

17. A method for producing a gemstone testing apparatus, the method comprising
 providing a transparent housing portion with a detector probe,
 coating an interior surface of a reflector housing with a light reflective layer,
 attaching the transparent housing portion to the reflector housing,
 providing an apparatus body,
 connecting an UV light emitter to electronic circuitry of the apparatus body,
 connecting the detector probe to the electronic circuitry,
 attaching the reflector housing to the apparatus body.

| LISTING OF REFERENCE NUMERALS | |
| --- | --- |
| 9 | catch |
| 10 | gemstone testing apparatus |
| 11 | head region |
| 12 | apparatus body |
| 13 | cylindrical reflector portion |
| 14 | transparent cylindrical portion |
| 15 | detector probe |
| 16 | indicator/display region |
| 17 | grip indentations |
| 18 | top surface |
| 19 | side/lateral surface |
| 20 | display panel |
| 21 | indicator lights |
| 26 | printed circuit board |

-continued

LISTING OF REFERENCE NUMERALS

| | |
|---|---|
| 27 | UV LED |
| 28 | inner surface |
| 29 | back surface |
| 30 | direct illumination region |
| 31 | reflected light beam |
| 32 | infrared transmitting LED |
| 33 | buzzer |
| 34 | microcontroller |
| 35 | on/off switch |
| 36 | power source |
| 37 | Thermocouple Amp |
| 38 | Electrical Conductivity |
| 39 | Metal Detector |
| 40 | method step |
| 41 | testing step |
| 42 | decision step |
| 43 | display step |
| 44 | method step |
| 45 | testing step |
| 46 | decision step |
| 47 | display step |
| 48 | display step |
| 51 | Heater Control & Driver |
| 52 | Low Battery Detector |

What is claimed is:

1. A gemstone testing apparatus comprising:
an apparatus body enclosing electronic circuitry;
a visible violet light emitter configured to generate visible violet light;
a reflector housing, an interior surface of the reflector housing being provided with a light reflective layer;
a transparent housing portion provided adjacent to the reflector housing; and
a detector probe protruding from the transparent housing portion,
wherein the visible violet light emitter is provided within the reflector housing and the reflector housing is provided for directing the visible violet light of the visible violet light emitter through the transparent housing portion into the vicinity of a tip of the detector probe,
wherein the detector probe and the visible violet light emitter are connected to the electronic circuitry, and
wherein the electronic circuitry comprises a conductivity sensing circuitry that is connected to the detector probe and to a processing unit, the processing unit being operative to turn on the visible violet light emitter and to perform a subsequent conductivity measurement using the conductivity sensing circuitry.

2. The gemstone testing apparatus of claim 1, wherein the visible violet light emitter is configured to emit light in the visible violet and blue spectrum.

3. The gemstone testing apparatus of claim 1, wherein the visible violet light emitter is configured to emit light with a wavelength of 390 nm to 450 nm.

4. The gemstone testing apparatus of claim 1, wherein the detector probe is provided at an end portion of the transparent housing portion.

5. The gemstone testing apparatus of claim 1, wherein a back surface of a chamber defined by the transparent housing portion, the reflector housing, and the apparatus body is provided with a light reflective layer.

6. The gemstone testing apparatus of claim 1, wherein the interior surface of the reflector housing is substantially entirely covered with the light reflective layer.

7. The gemstone testing apparatus of claim 1, wherein the light reflective layer is provided by electroplating.

8. The gemstone testing apparatus of claim 1, further comprising a display region that is connected to the processing unit.

9. The gemstone testing apparatus of claim 8, wherein the display region comprises indicator LEDs.

10. The gemstone testing apparatus of claim 8, wherein the display region comprises an LCD.

11. The gemstone testing apparatus of claim 1, wherein the visible violet light emitter is positioned at a distance from other parts of the gemstone testing apparatus.

12. The gemstone testing apparatus of claim 1, wherein the transparent housing portion is conically tapered from the reflector housing towards a tip end of the transparent housing portion.

13. The gemstone testing apparatus of claim 1, wherein the reflector housing is conically tapered from the apparatus body towards the transparent housing portion.

14. The gemstone testing apparatus of claim 1, wherein a longitudinal dimension of the reflector housing is at least three times as long as a longitudinal dimension of the transparent housing portion.

15. The gemstone testing apparatus of claim 1, wherein the electronic circuitry comprises a temperature sensing circuitry connected to the detector probe and to the processing unit.

16. A head portion for a gemstone testing apparatus, the head portion comprising:
a reflector housing, an interior surface of the reflector housing being provided with a light reflective layer;
a transparent housing portion attached to the reflector housing;
a detector probe protruding from the transparent housing portion, the detector probe having connections for connecting to electronic circuitry of the gemstone testing apparatus; and
a visible violet light emitter within the reflector housing, the visible violet light emitter having connections for connecting to the electronic circuitry.

17. A method for producing a gemstone testing apparatus, the method comprising steps of:
providing a transparent housing portion with a detector probe;
coating an interior surface of a reflector housing with a light reflective layer;
attaching the transparent housing portion to the reflector housing;
providing an apparatus body;
connecting a visible violet light emitter to electronic circuitry of the apparatus body;
connecting the detector probe to the electronic circuitry; and
attaching the reflector housing to the apparatus body.

* * * * *